United States Patent
Merritt et al.

(10) Patent No.: US 9,402,691 B2
(45) Date of Patent: Aug. 2, 2016

(54) SYSTEM FOR DETERMINING AND TRACKING MOVEMENT DURING A MEDICAL PROCEDURE

(71) Applicant: X-NAV Technologies, LLC, Lansdale, PA (US)

(72) Inventors: Scott A. Merritt, Green Lane, PA (US); Robert W. Emery, III, McLean, VA (US); Edward J. Marandola, Gwynedd, PA (US); Christopher W. Scharff, Collegeville, PA (US)

(73) Assignee: X-Nav Technologies, LLC, Lansdale, PA (US)

( * ) Notice: Subject to any disclaimer, the term of this patent is extended or adjusted under 35 U.S.C. 154(b) by 0 days.

(21) Appl. No.: 14/487,987

(22) Filed: Sep. 16, 2014

(65) Prior Publication Data

US 2016/0074129 A1   Mar. 17, 2016

(51) Int. Cl.
| | | |
|---|---|---|
| G06K 9/00 | (2006.01) | |
| A61B 19/00 | (2006.01) | |
| A61B 5/00 | (2006.01) | |
| A61B 6/14 | (2006.01) | |
| A61C 1/08 | (2006.01) | |
| A61C 9/00 | (2006.01) | |

(52) U.S. Cl.
CPC .............. *A61B 19/54* (2013.01); *A61B 5/0077* (2013.01); *A61B 6/14* (2013.01); *A61C 1/082* (2013.01); *A61C 9/0046* (2013.01); *A61B 2019/5437* (2013.01); *A61B 2019/5466* (2013.01); *A61B 2034/2055* (2016.02); *A61B 2090/3983* (2016.02)

(58) Field of Classification Search
None
See application file for complete search history.

(56) References Cited

U.S. PATENT DOCUMENTS

| | | |
|---|---|---|
| 3,878,610 A | 4/1975 | Coscina |
| 5,588,430 A | 12/1996 | Bova et al. |
| 5,772,432 A | 6/1998 | Jordan et al. |
| 5,823,958 A | 10/1998 | Truppe |

(Continued)

FOREIGN PATENT DOCUMENTS

| | | |
|---|---|---|
| DE | 19902273 A1 | 8/2000 |
| EP | 0501993 B1 | 11/1997 |

(Continued)

OTHER PUBLICATIONS

Harris et al., A Combined Corner and Edge Detector, AVC 1988 doi:10.5244/C.2.23, 147-151, Plessey Research Roke Manor, UK (1988).

(Continued)

*Primary Examiner* — Stephen R Koziol
*Assistant Examiner* — Delomia L Gilliard
(74) *Attorney, Agent, or Firm* — Drinker Biddle & Reath LLP

(57) ABSTRACT

An image guidance system for tracking a surgical instrument during a surgical procedure. The image guidance system includes a plurality of cameras adapted to be located external to a surgical area for capturing images of optically visible patterns. A processing system receives and processes the images to recognize the patterns and triangulate the locations and orientations of each pattern relative to a camera. The processing system uses a reference dataset which defines a reference coordinate system based on alignment to a portion of the oral anatomy. The processing system determines the location and orientation of the tracked instrument based on the reference dataset.

19 Claims, 15 Drawing Sheets

(56) References Cited

U.S. PATENT DOCUMENTS

| | | |
|---|---|---|
| 6,018,592 A | 1/2000 | Shinagawa et al. |
| 6,072,903 A | 6/2000 | Maki et al. |
| 6,096,048 A | 8/2000 | Howard, III et al. |
| 6,223,067 B1 | 4/2001 | Vilsmeier et al. |
| 6,368,285 B1 | 4/2002 | Osadchy et al. |
| 6,611,141 B1 | 8/2003 | Schulz et al. |
| 6,640,128 B2 | 10/2003 | Vilsmeier et al. |
| 6,978,167 B2 | 12/2005 | Dekel et al. |
| 7,457,443 B2 | 11/2008 | Persky |
| 7,762,814 B2 | 7/2010 | van der Zel |
| 7,889,905 B2 | 2/2011 | Higgins et al. |
| 7,894,878 B2 | 2/2011 | Noujeim |
| 8,064,669 B2 | 11/2011 | Higgins et al. |
| 8,172,573 B2 | 5/2012 | Sonenfeld et al. |
| 8,218,905 B2 | 7/2012 | Dekel et al. |
| 8,376,738 B2 | 2/2013 | Wagner |
| 8,938,282 B2 | 1/2015 | Daon |
| 2003/0156681 A1 | 8/2003 | Cianciosi et al. |
| 2004/0068263 A1 | 4/2004 | Chouinard et al. |
| 2005/0085714 A1 | 4/2005 | Foley et al. |
| 2006/0083422 A1 | 4/2006 | Ernst et al. |
| 2006/0257817 A1 | 11/2006 | Shelton |
| 2007/0106152 A1 | 5/2007 | Kantrowitz et al. |
| 2007/0173790 A1 | 7/2007 | Moctezuma De La Barrera et al. |
| 2008/0019579 A1 | 1/2008 | Crucs |
| 2008/0039717 A1 | 2/2008 | Frigg et al. |
| 2009/0209852 A1 | 8/2009 | Mate et al. |
| 2009/0306499 A1 | 12/2009 | Van Vorhis et al. |
| 2010/0075273 A1 | 3/2010 | Karlsson et al. |
| 2010/0233647 A1 | 9/2010 | Yang |
| 2010/0286568 A1 | 11/2010 | Xia et al. |
| 2011/0008751 A1 | 1/2011 | Pettersson |
| 2011/0217667 A1 | 9/2011 | Groscurth et al. |
| 2012/0015329 A1* | 1/2012 | Gross ............... A61C 1/084 433/215 |
| 2012/0046536 A1 | 2/2012 | Cheung et al. |
| 2012/0230567 A1 | 9/2012 | Greenberg |
| 2012/0316486 A1 | 12/2012 | Cheung et al. |
| 2013/0322719 A1 | 12/2013 | Dekel et al. |
| 2014/0147807 A1 | 5/2014 | Yau et al. |
| 2014/0236159 A1* | 8/2014 | Haider ............... A61B 19/5244 606/88 |

FOREIGN PATENT DOCUMENTS

| | | |
|---|---|---|
| EP | 1527417 B1 | 5/2005 |
| GB | 2246261 A | 1/1992 |
| WO | 0119273 A1 | 3/2001 |
| WO | 2012068679 A1 | 5/2012 |
| WO | WO2015048994 A1 | 4/2015 |

OTHER PUBLICATIONS

Harris et al., "A Combined Corner and Edge Detector", Plessey Research Roke Manor, The Plessey Company PLC, UK, 1988, pp. 147-151.

CT Scan Protocol, 5-IG-0407, Image Navigation Ltd., Jun. 2008, 16 pages.

Fenlon et al., "Locking acrylic resin dental stent for image-guided surgery", The Journal of Prosthetic Dentistry, vol. 83, No. 4, Apr. 2000, 4 pages.

James E. Eckhart, DDS, "Comparisons of Oral Devices for Snoring", The Journal of the California Dental Assoc., Aug. 1998, 15 pages.

Widmann et al., "In vitro accuracy of a novel registration and targeting technique for image-guided template production", Clin. Oral Impl. Res., Jul. 27, 2004, 6 pages.

Notice of Transmittal of the International Search Report and the Written Opinion, ISA, Oct. 1, 2014, 25 pages.

Partial Search Report, EP Appl. No. 15185062.5 (Mar. 3, 2016).

Dubrofsky, Homography Estimation, B.Sc., Careleton University, 2007, The University of British Columbia, Vancouver, Mar. 2009, 32 pages.

Brown, A Survey of Image Registration Techniques, ACM Computing Surveys, vol. 24, No. 4, Dec. 1992, pp. 325-376.

Shu, Automatic Grid Finding in Calibration Patterns Using Delaunay Triangulation, NRC/ERB-1104, Aug. 22, 2003, 17 pages.

* cited by examiner

SYSTEM FOR DETERMINING AND TRACKING MOVEMENT DURING A MEDICAL PROCEDURE

RELATED APPLICATION

This Application is related to co-pending application Ser. No. 14/488,004, filed on Sep. 16, 2014.

FIELD OF THE INVENTION

The present invention relates to a system for image guided surgery and, more particularly, to an system for determining and tracking movement during a medical procedure using an externally visible reference point.

BACKGROUND

Image guided surgery has had extensive developments over the years and is now a very important tool in surgical procedures. Most of the developments have centered around imaging locations in the body where there is very little access, such as internal organs.

Oral surgery, which is defined herein as any surgery occurring within the oral cavity, can be just as difficult to conduct visually. The oral cavity is relatively small and difficult for a patient to maintain open for prolonged periods of time. Even if a surgical site is visible, once the drill penetrates, it becomes difficult to determine where the tip is at any given time.

Image guided surgery involves the use of a computed or computerized axial tomography scan, commonly referred to as CT or CAT scans, to create a digital image of the surgical site (typically in three dimensions). The surgeon then creates a plan for the surgery using the image. During surgery, the image generated from the prior CT scan is used in conjunction with a special instrument, to visually depict where the tip of the instrument is inside the patient.

In order to do so, the digital image from the scan must be accurately registered to the surgical site of the patient such that movement of the patient causes adjustment of the digital image. The exact location of the instrument tip relative to the patient must also be known.

For oral surgery, such as during dental implant placement, a doctor has to drill in free space while controlling the drill in six degrees of freedom with the patient potentially moving. This makes accurately drilling into good bone while avoiding roots and nerves very difficult. As such, image guided surgery has recently been used to facilitate the drilling process. CT scans of the patient's teeth are used by the doctors to accurately determine bone density, width and height, as well as understand relationships of other teeth and anatomical structures in order to plan a surgical event to provide the restorative solution that would likely be the most successful and least traumatic.

Planning software and fabrication systems exists today that uses the CT image to assist in translating a pre-surgical plan to a passive surgical guide, i.e., creating a virtual plan for the surgery and then prefabricating in the dental laboratory a surgical guide to implement the plan. These passive surgical guides help accurately direct the doctor to the proper location, angle and depth. Passive image guided surgery has limitations. They must be fabricated prior to surgery in a dental lab or by a guide manufacturer. This requires greater doctor and patient time and expense. If there is a change in a patients mouth or the doctor desires to change the plan, the guide is no longer useful. In many cases the patient is unable to open their mouth wide enough to accommodate the instruments needed and the guide.

Active image guided surgery solves many of the problems of passively guided systems, i.e., limited maximal mouth opening, the need to prefabricate a passive guide and the inability to change the plan during surgery can be overcome by actively guided systems. In order to provide active image guided surgery, the position of the patient's mouth, specifically the bone and teeth, must be accurately tracked and registered to the scanned image and the surgical tool. In order to do so, most conventional systems require the creation of a registration device that is attached to the patient's head or inserted into the mouth which includes fiducial markers and a sensor. Some registration devices are attached to the outside of the head, for example, a head mounted fixture. Others involve a fixture that is attached to the jawbone with the sensors located outside the mouth in order to limit the interference with the surgical zone and to permit optical sensors to track the movement of the fixture and surgical tool.

In order to create the oral fixture, an impression is taken, typically of both the upper and lower sets of teeth weeks in advance of the operation. The impression is then sent to a lab where a cast is made substantially duplicating the teeth. From the cast an oral fixture is made that either seats on the teeth or is designed to be drilled into the jawbone. The fixture includes at least the fiducial markers and also, if not fitted with a sensor, includes mounting locations for the optical sensors.

After the lab creates the fixture it is sent back to the dental surgeon. The patient is brought in, fitted with the fixture and a CT scan is taken. The patient is once again sent home. A digital image of the patient's oral cavity is created from the scan and the surgeon develops the surgical plan.

The patient is then brought in for the operation. The fixture is attached to the patient. Optical transmitters are located about the patient and emit signals that are detected by the sensor(s). The sensor(s) send a signal to the software as the patient's mouth moves and an adjustment is made to the digital image of the patient's oral cavity. The software also tracks the position of the instrument and depicts an image of the instrument in the proper location relative to the digital image of the teeth.

In addition to the inconvenience to the patient, existing systems tend to have some difficult accurately registering the patient to the digital scan. All present dental active image-guided surgery systems involve the use of optical tracking which requires that the fixture that is placed in the patient's mouth extends outside the mouth in order to be detected by the optical transmitter or receivers.

SUMMARY OF THE INVENTION

An image guidance system is disclosed for tracking a surgical instrument during oral surgery. The system includes a fixture configured to be removably attached to a patient's anatomy in a location near a surgical area.

A first tracking assembly, including a bracket assembly, is removably attached to the fixture. The first tracking assembly includes a first tracking pattern surface including a first optically visible pattern. The bracket assembly positions the first tracking pattern at a location spaced apart from the surgical area.

The system includes a tool for use in the surgical procedure. A second tracking assembly is attached to the tool and includes a second tracking pattern surface. The second tracking pattern surface includes a second optically visible pattern.

A plurality of cameras are mounted away from the surgical area at a position that permits the cameras, when activated, to capture images of the optically visible patterns on the first and second tracking pattern surfaces.

A processing system is connected to the cameras and processes the captured images. The processor is configured to recognize the optically visible patterns and triangulate the locations and orientations of the first and second tracking assemblies. The processing system determines the location and orientation of the tracked tool based on a reference dataset that includes the location and orientation of the fixture with respect to a CT scan. The processing system analyzing relative transforms between each camera of the optically visible patterns on the first and second tracking pattern surfaces.

The fixture is preferably configured to removably attach to one or more teeth in a patient's mouth.

The bracket assembly includes a bracket mount that removably attaches to flanges on the fixture. The bracket assembly also includes a tracking mount that attaches to the first tracking pattern surface, and a support arm that attaches the bracket mount to the tracking mount. The bracket mount preferably includes two spaced apart mounting posts that engage with the flanges. vvThe attachment of the tracking mount to the first tracking pattern surface is preferably adjustable.

In one embodiment, the tracking mount includes a base with a series of indentations and protrusions. The first tracking assembly includes a frame which attaches to the tracking mount so as to be adjustably oriented with respect to the bracket assembly. The frame may include a series of indentations and protrusions that are configured to mate with the indentations and protrusions on the tracking mount so as to permit rotation of the tracking frame relative to the base.

The optically visible patterns each preferably contain a plurality of 2D contrasting shapes, the contrasting shapes arranged so as to uniquely differentiate each optically visible pattern from the other optically visible pattern.

Each camera is located so as to capture an image of each optically visible pattern which is at a different viewing angle than the image of the same optically visible pattern captured by the other camera(s). The cameras send data representing the 2D images of the optically visible patterns.

The reference data includes location data for contrasting shapes on a plurality of patterns. The processor uses the reference data to determine the specific pattern in the image.

The foregoing and other features of the invention and advantages of the present invention will become more apparent in light of the following detailed description of the preferred embodiments, as illustrated in the accompanying figures. As will be realized, the invention is capable of modifications in various respects, all without departing from the invention. Accordingly, the drawings and the description are to be regarded as illustrative in nature, and not as restrictive.

BRIEF DESCRIPTION OF THE DRAWINGS

For the purpose of illustrating the invention, the drawings show a form of the invention which is presently preferred. However, it should be understood that this invention is not limited to the precise arrangements and instrumentalities shown in the drawings.

DESCRIPTION OF THE PREFERRED EMBODIMENTS

Figure 1:
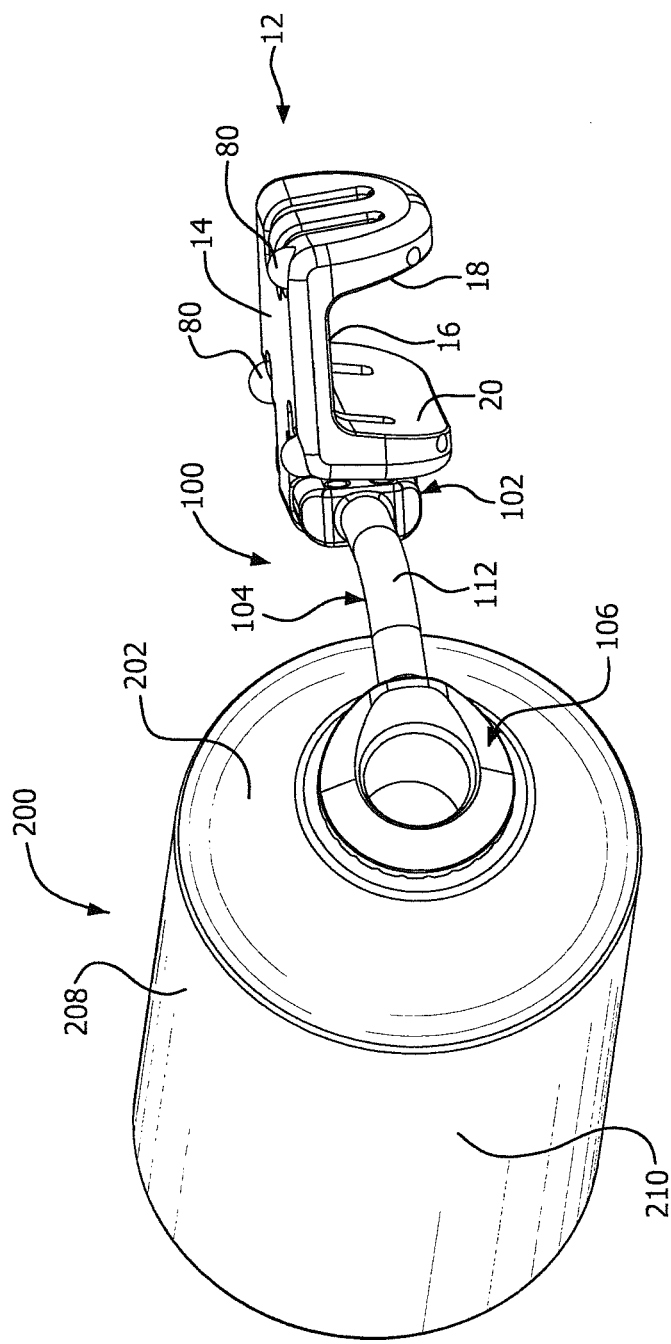
FIG. 1 is a perspective view of a tracking assembly with a pattern display surface attached to an oral fixture for use in an embodiment of the present invention.

The present invention addresses the prior art deficiencies by providing an image guidance system for efficiently tracking a patient's movement during surgery. The present invention will be described as it related to oral surgery and the tracking of the movement of a patient's mouth, but the invention is not necessarily limited to that embodiment. In one embodiment, the image guidance system includes a plurality of cameras located outside the oral cavity to provide images of optically visible patterns attached to the patient through an oral fixture and that are located external to the area being operated on. The images are used to detect and tracking movement of the patient's mouth, and/or a surgical instrument or tool. A processing system receives and processes the images to recognize patterns and triangulate the locations and orientations relative to each camera. The processing system uses a reference dataset which defines a reference coordinate system based on alignment to a portion of the oral anatomy. The processing system determines the location and orientation of the tracked surgical instrument and the oral fixture based on the reference dataset.

Turning now to the figures, embodiments of the image guidance system 10 are shown for use in an oral surgical procedure. As will become apparent, the inventive features are not limited to oral surgical procedures and have applicability to other surgical procedures. In one embodiment the system 10 includes an oral dental appliance or fixture 12 that is designed to attach to one or more teeth of the patient. One suitable fixture is described in co-pending application Ser. No. 14/209,500, the disclosure of which is incorporated herein by reference in its entirety. Details of the fixture 12 as referenced herein can be found in that application. The fixture 12 is preferably removably attachable to the patient's teeth and includes a support 14 that is made from a suitably strong material, preferably a thermoset plastic material, that is sufficiently rigid so as not to deform when subjected to the elevated temperatures discussed below. In one embodiment, the plastic material is polyphenylsulphone or acetal copolymer. The support 14 includes a base 16 that is, preferably, generally planar, with an inner wall 18 and an outer wall 20. The inner wall 18 and outer wall 20 are attached to and extend outward from the base 16. Preferably the walls 18, 20 extend outward from the base 16 at substantially or generally right angles from the base 16. However as will be appreciated the walls could be at other desired angles from the base 16. The walls and base are preferably formed as an integral component. The spacing of the inner and outer walls 18, 20 is larger than the width of the teeth to which the oral fixture 12 is intended to be attached. It should be readily apparent that the spacing of the walls 18, 20 can be different between fixtures designed for adults and children. The walls 18, 20 preferably have a height from the base which extends below the top of the patient's teeth when installed. Preferably the height is sufficient to extend about 10 mm to about 13.5 mm down from occlusal surface when installed on a patient's tooth with the overlying material.

As described in co-pending application Ser. No. 14/209,500, the oral fixture 12 also includes a moldable thermoplastic material located on an inner surface of the support 14, preferably on the base 16. The moldable material is designed to form an impression of a portion of a patient's teeth. More specifically, when the moldable material is in its uncured (unset) state, the material is "activated" by placing the oral fixture 12 (support 14 with moldable material on it) into a bowl of warm or hot water that is at a temperature above which the material begins to become moldable. Preferably the chosen material has a characteristic that provides the user with a visual indication that the material is ready to be molded, such as changing color (e.g., from white to clear or translucent). Once the material is activated, the oral fixture 12 is placed on a patient's teeth and slight downward pressure is applied causing the moldable material to deform around the top and at least some of the sides of the teeth between the support walls 18, 20. After a prescribed period of time, generally about 30 seconds to one minute, the moldable material sets to form an impression of the outside shape and contours of the teeth that were covered by the material. The oral fixture 12 can then be removed from the patient's mouth. Further curing can be achieved by placing the oral fixture 12 with the mold material into a bowl of cold or ice water to complete the setting process.

The material selected must remain solid (cured) at temperatures typically existing in a person's mouth (generally, around 100 degrees F.), and moldable at a temperature above that (e.g., above 130 degrees F.), at least until it is initially set. The material should be sufficiently rigid in its cured state so as to maintain the shape of the impression without distorting. Suitable thermoplastic materials for use in the invention includes Polycaprolactone or Polyvinylsiloxane (PVS). However, any type of moldable material that can set and retain an impression can be used in the present invention. The moldable material may be flavored to please the patient during the molding process. The amount of material used will vary depending on the number and size of teeth that are to be molded.

The oral fixture 12 also includes a plurality of fiducial markers 80 mounted on the support 14 in order for the system to determine where the oral fixture 12 (and thus the camera) is relative to the patient's teeth. The markers 80 are at certain locations on the fixture 12 and are part of a registration system for properly locating the fixture 12 in space. As will be discussed in more detail below, the fiducial markers are detected during a CT scan of the patient's mouth and their location is registered in the scan. There are preferably at least three fiducial markers 80 spaced apart from each other and rigidly attached to the support 14. The use of the three fiducial markers permits location of oral fixture in three dimensions. The fiducial markers may be located on the base 16 and/or the walls 18, 20.

The fiducial markers 80 may be spherical in shape and/or colored so as to be easily detected by a technician or doctor, as well as the software being used. More specifically, in order for the fiducial markers 80 to be detected in a scanned image, the fiducial markers 80 must have a different radiodensity (i.e., the density that is detected by the CT scan) than the fixture, moldable material and teeth. In one embodiment, the fiducial markers 80 are ceramic ball bearings. However, other materials, shapes and sizes may be used. Preferably the fiducial markers 80 each have their own radiodensity or are of different sizes or shapes so that a software program can be used to automatically detect the different fiducial markers 80 in the scanned image. The software may also apply a color in the scanned image that corresponds to the markers color or shape to assist in registration of the oral fixture 12 as will be discussed further below. It is also contemplated that the fiducials can include passive optical attributes, such as specular or diffuse surfaces, or active optical attributes, such as light emitting materials, for use in visually locating the fiducials relative to a camera or other location.

While the preferred fiducial markers are distinguished from the teeth and oral fixture 12 by their radiodensity, it is also contemplated that other distinguishing features can be used other than density. For example, the markers can be pre-fixed transmitters or other position location devices.

The oral fixture 12 also includes at least one mount 26 attached to or formed integral with the support 14. In the illustrated embodiment, the mount 26 extends outward from the outer wall 20. As will be discussed below, the mount 26 is configured to have a tracking assembly 200 attached to it for use in tracking motion (position changes) of the fixture 12. In one embodiment, the mount 26 includes at least one flange 28 and more preferably two spaced apart flanges 28, 30 that extend out of the side of the fixture 12. Each flange 28, 30 may include notches or indentations 32 formed in the opposite lateral sides of the flange 28, 30.

A bracket assembly 100 is removably attachable to the mount 26 of the oral fixture 12 and is configured to hold the tracking assembly 200. In the illustrated embodiment, the bracket assembly includes a bracket mount 102 that removably attaches to the flanges 28, 30 on the fixture, a support arm 104, and a tracking mount 106. The bracket mount 102 includes two spaced apart mounting posts 108$_A$, 108$_B$. Each mounting post 108 preferably includes a protrusion 110 that is configured to engage with and sit in the notch 32 such that the mounting posts 108$_A$, 108$_B$ are positioned on either side of and against the flanges 28, 30.

Figure 6:
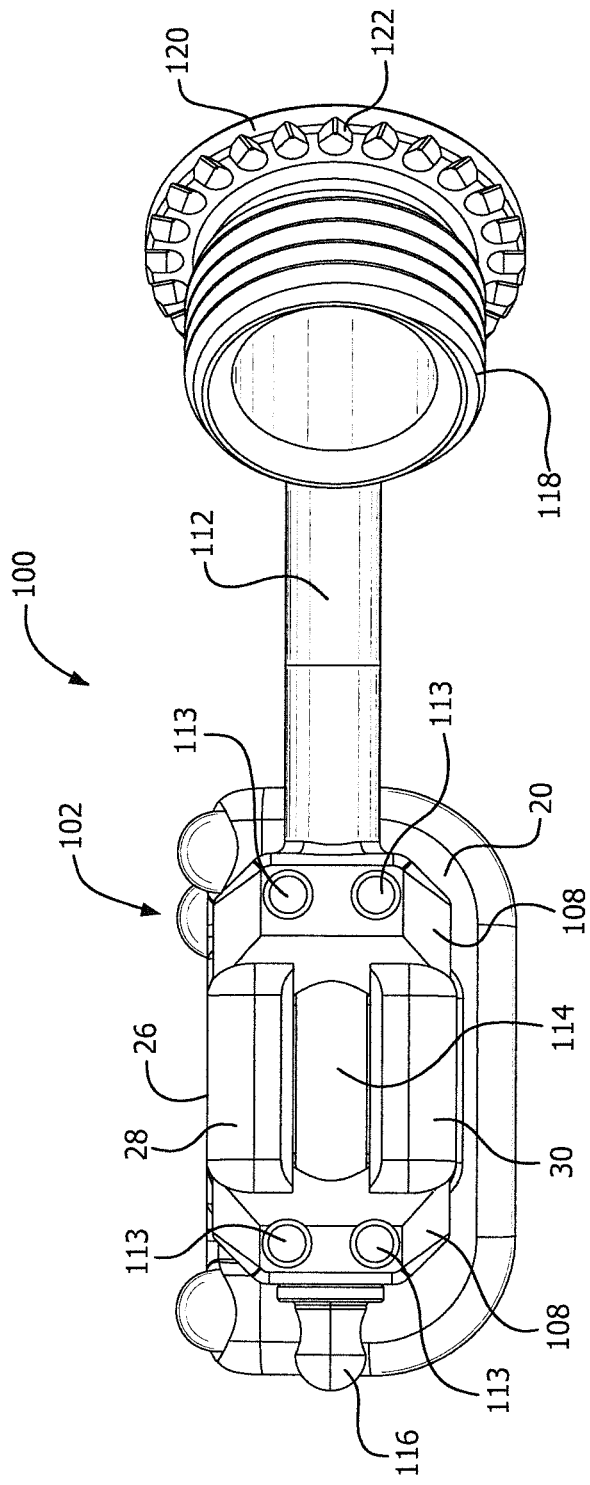
FIG. 6 is a different side view of the bracket of FIG. 5.

The support arm 104 includes a main portion 112 and a fixture portion 114 that extends between the posts 108$_A$, 108$_B$. In one embodiment, the support arm 104 is rigidly, preferably fixedly, attached to one of the posts 108$_A$. The other post 108$_B$ (the one furthest from the main portion 112) is preferably slidably disposed on the fixture portion 114 so that the spacing between the posts 108$_A$, 108$_B$ is adjustable. A distal end of the fixture portion 114 extends through the post 108$_B$. Threads (not shown) are preferably formed on the distal end of the fixture portion 114. A knob 116 is threaded onto the distal end of the fixture portion. As shown in FIG. 6, tracker arm pins 113 are used to attach the posts 108 captive on the support arm 112. This allows the posts 108 to rotate freely about the support arm 112. When mounted to the fixture 12, post 108$_A$ is positioned against the flanges 28, 30 so that the protruding portion 110 seats in the notch 32. The other post 108$_B$ is slid on the distal end of the fixture portion of the support arm 104 until its protruding portion 110 seats within the other notch 32. The knob 116 is tightened, thereby securing the arm 104 to the oral fixture 12. It should be readily apparent that the posts 108 could, instead, include notched portions and the flanges 28, 30 could have protruding portions, or the posts and flanges might simply have flush mounting surfaces.

As discussed above, the opposite end of the arm 104 includes a tracking mount 106 for attaching a fixture tracking assembly 200. In the illustrated embodiment, the tracking mount 106 includes a threaded stub 118 and a base 120. The base 120 preferably has a series of teeth or indentations and protrusions 122. The base 120 and threaded stub 118 are preferably integral with the main portion 112 of the arm 104.

Figure 4:
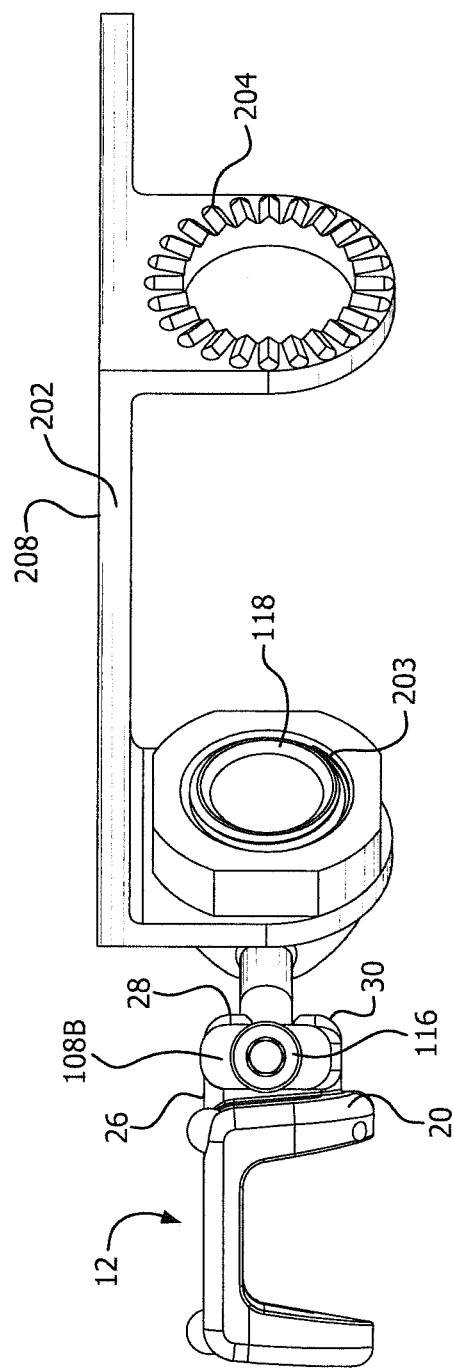
FIG. 4 is a side view of the oral fixture and tracking assembly of FIG. 3.
Figure 5:
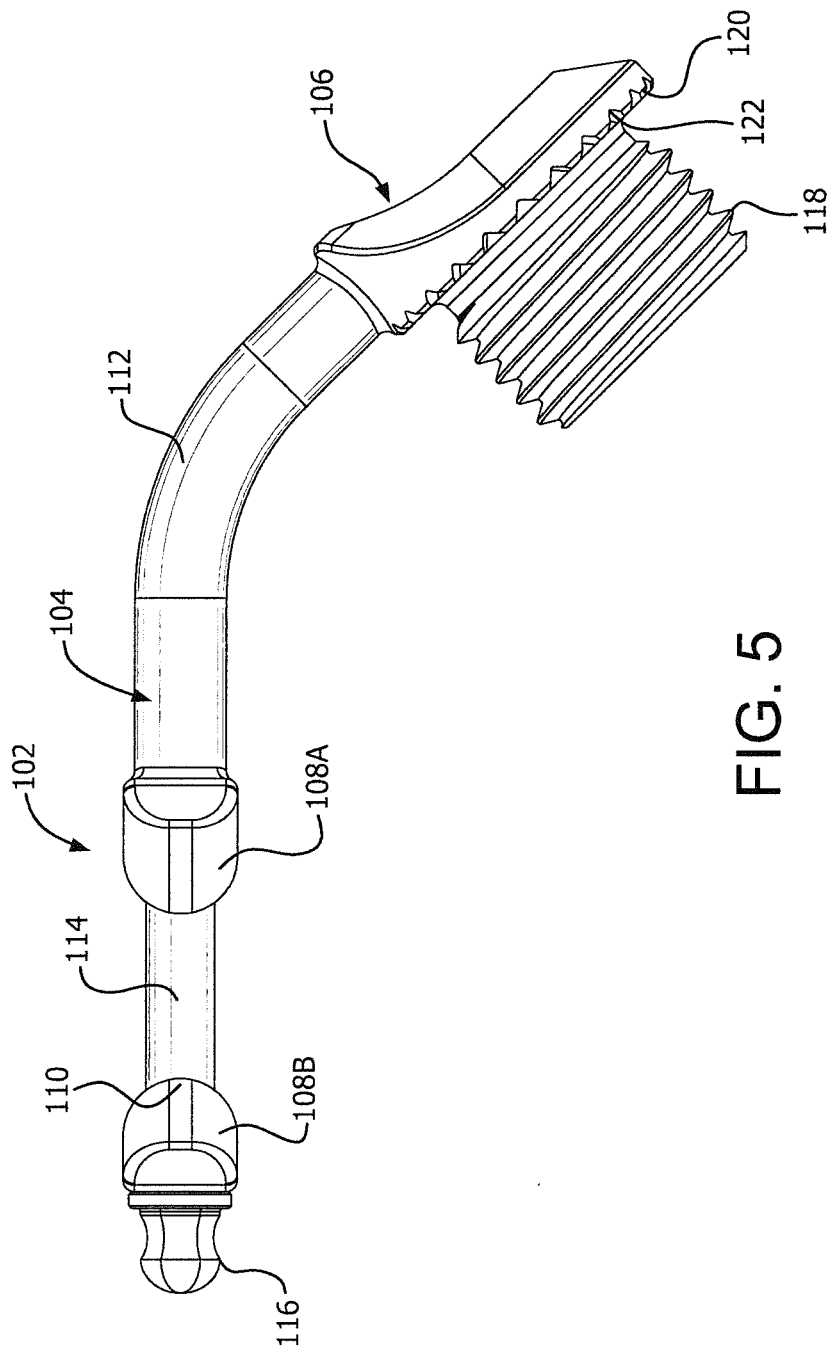
FIG. 5 is a side view of a bracket for attaching a tracking assembly to an oral fixture according to the present invention.

The fixture tracking assembly 200 is attached to the tracking mount 106 so that it is preferably adjustable. More particular, the fixture tracking assembly 200 includes a frame 202 which attaches to the tracking mount 106 of the bracket assembly 100. The attachment is preferably configured to permit the frame to adjustably oriented with respect to the bracket assembly 100 as will be discussed in more detail. In the illustrated embodiment, the frame 202 includes a hole 203 (shown in FIG. 4) with threads that threadingly engage with the threads on the stub 118 of the arm 104. Preferably there are a series of teeth or indentations and protrusions 204 that are configured to mate with the teeth or indentations and protrusions 122 on the bracket assembly 100. The inclusion of the mating teeth 122/204 permits accurate and repeatable adjustability of the position of the frame 202 relative to the support arm 104. In the illustrated embodiment, the mounting of the fixture tracking assembly 200 to the bracket assembly 100 permits the tracking assembly to be lockably positioned at different positions of rotation about axis 206.

The tracking assembly includes a pattern display surface 208 that is attached to or formed on the frame 202. By adjusting the attachment of the fixture tracking assembly 200 to the bracket assembly 100, it is possible to change the orientation of the pattern display surface 208 about the axis 206. This is a beneficial feature since it permits the pattern display surface 208 to be oriented at a suitable position during use so as to provide maximum detectability of the surface by externally mounted cameras.

Figure 2:
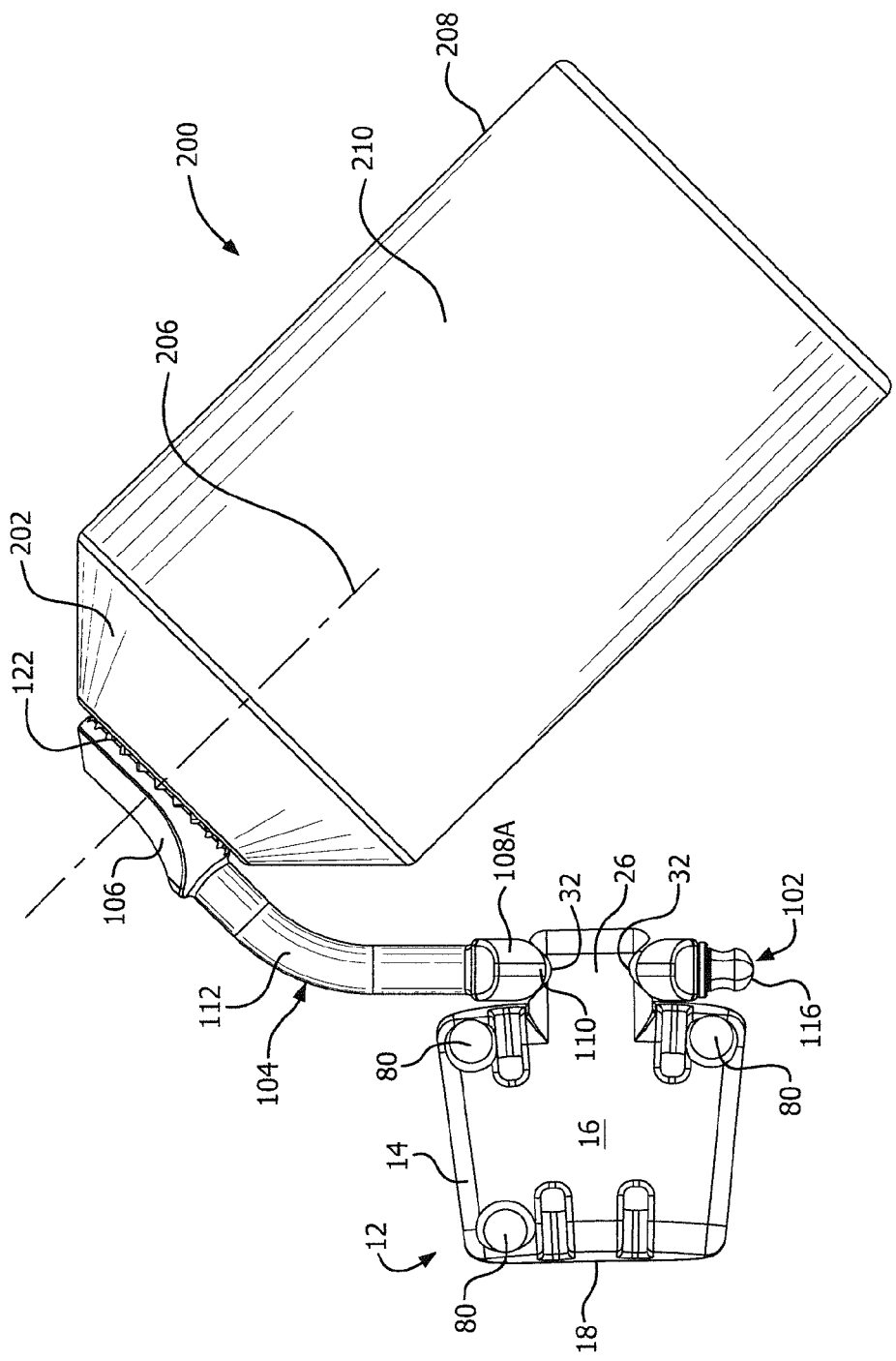
FIG. 2 is a top view of the oral fixture and tracking assembly of FIG. 1.

The pattern display surface can have any suitable shape. In one embodiment shown in FIGS. 1 and 2, the pattern display surface 208 of the tracking assembly is substantially cylindrical having an axis that is preferably collinear with the axis 206. In another embodiment shown in FIGS. 3 and 4, the pattern display surface 208 of the tracking assembly is substantially flat or planar. It should be readily apparent that any other shape could be used with the present invention.

Figure 10:
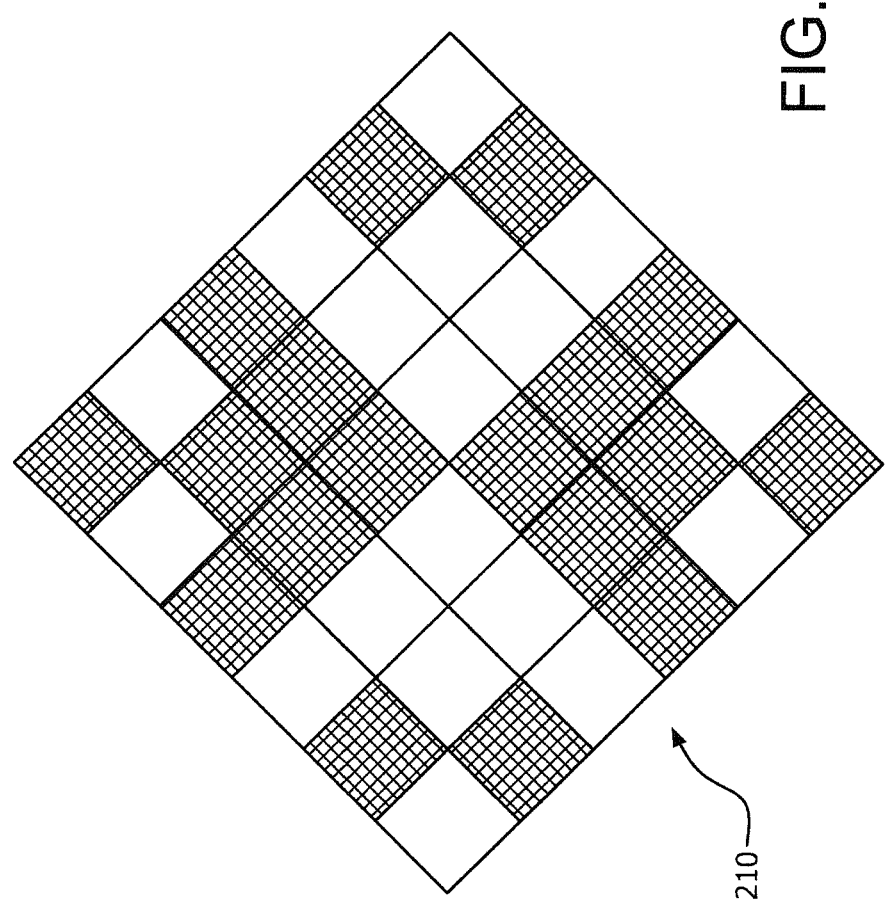
FIG. 10 is an illustration of one embodiment of a pattern for use on the pattern display surface of the tracking assembly.

A tracking pattern 210 is disposed or formed on the pattern display surface 208. The tracking pattern 210 is an optically visible pattern that is configured to provide visual reference points for externally mounted cameras to detect for use by a computer system to track the position and movement of the tracking assembly, and, thus, the oral fixture 12. In an embodiment, the tracking pattern may include a series of non-repetitive Quick Reference or QR Codes spaced apart on the surface of the tracking assembly 200. Application Ser. No. 14/209,500 describes some suitable tracking patterns that can be used in the present invention. FIG. 10 illustrates a 2D tracking pattern that may be used in the present invention.

Bar codes, Aztec codes or other 2D codes, or graphical images, could also be used. The pattern preferably uses contrasting colors, such as black (shown in dense cross-hatching) and white, to facilitate detection and recognition by the system. The arrangement of the checkerboard squares are arranged so as to be easily and quickly identified. It is also contemplated that other mechanisms can be used to provide the reference data needed, including LEDs, a data matrix, data glyphs, or raised or lowered features similar to braille. The tracking pattern 208 may be formed on a layer of material that is adhered to the frame of the tracking assembly. Alternatively, the tracking pattern may be molded or etched onto or disposed directly on the frame.

It is contemplated that the fixture tracking assembly 200 may be configured to provide backlighting or other mechanism to increase the contrast of the tracking pattern 210 in order to facilitate detection. If the tracking assembly is backlit, the tracking pattern 210 is preferably made of at least partially transparent or translucent material so as to enhance the contrast. It is also contemplated that a fluorescent material can be used to facilitate detection.

Figure 7:
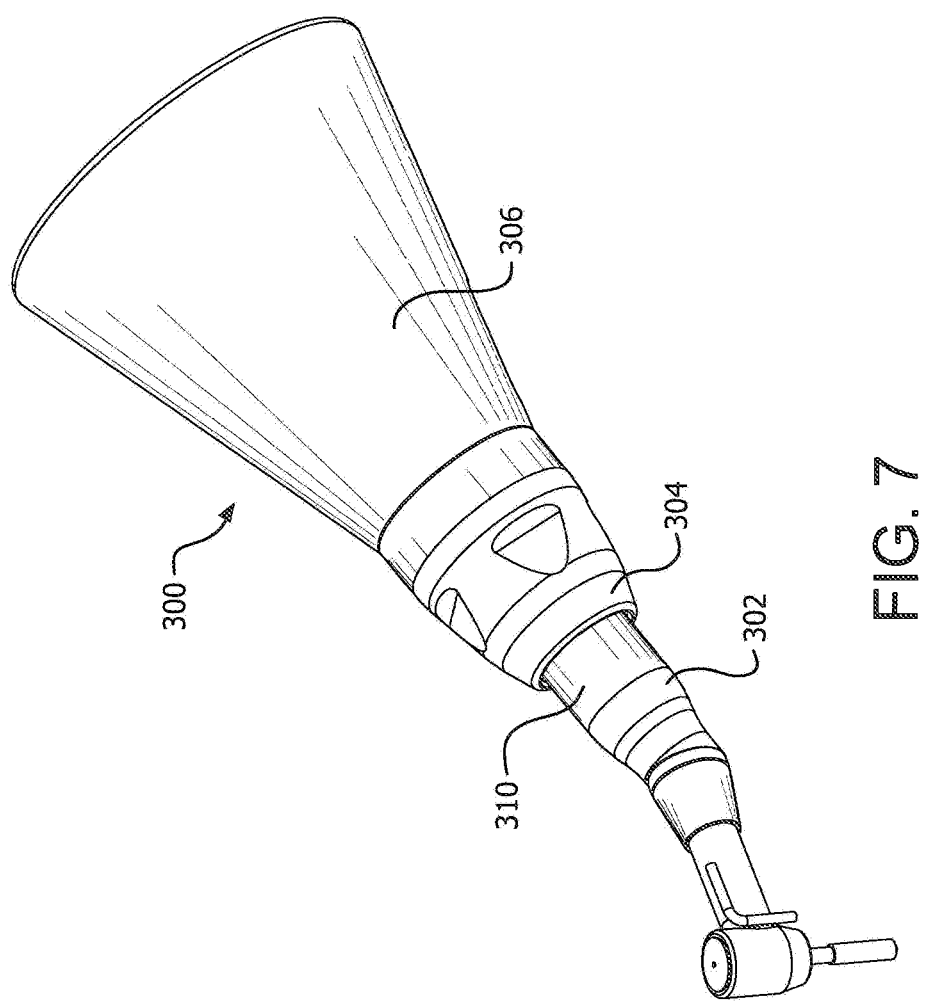
FIG. 7 is a perspective view of another embodiment of a tracking assembly attached to a dental instrument according to the present invention.
Figure 8:
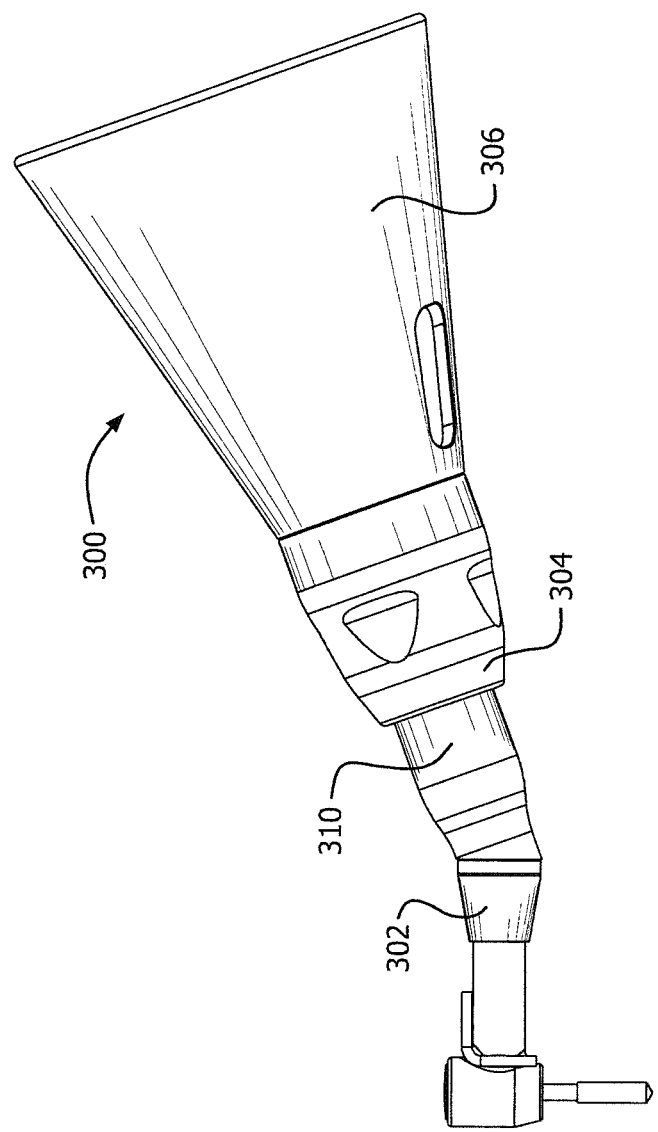
FIG. 8 is a side view of the dental instrument and tracking assembly of FIG. 7.
Figure 9:
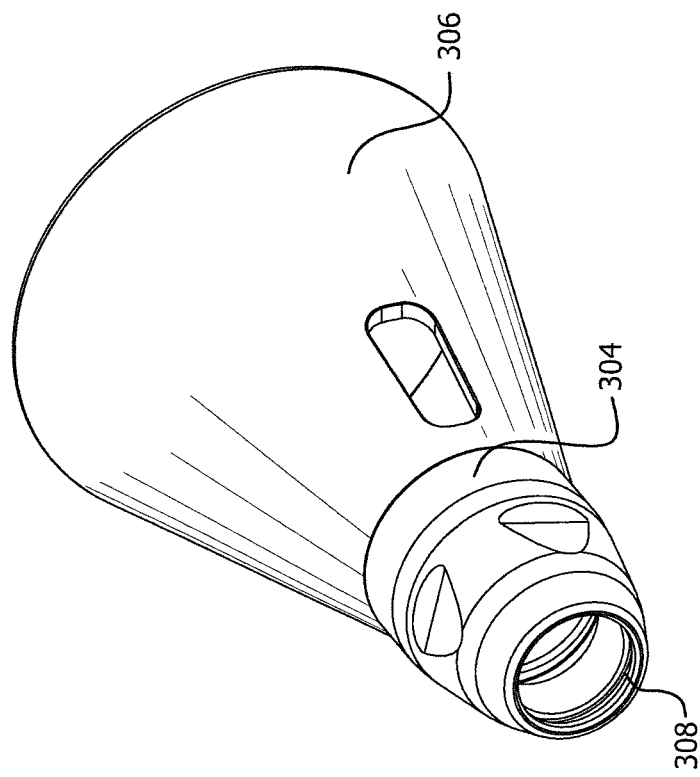
FIG. 9 is the tracking assembly of FIG. 7 removed from the dental instrument.

Referring now to FIGS. 7-9, a surgical tool tracking assembly 300 according to one embodiment is shown mounted to or part of a surgical dental tool 302, such as a drill. The tool tracking assembly 300 includes a tool mount 304 that is designed to secure a tool pattern surface 306 to the tool 302. The tool mount 304 includes an opening 308 that fits around the body 310 of the tool 302 in a secure manner so that the tracking assembly moves in combination with the surgical tool. The attachment could be through any of a number of different mechanisms well known in the art. For example, the tool tracking assembly is attached, for example, with a collet or similar well known mechanism which may be removably screwed on or clamped down on the tool body so as to secure the tool tracking assembly to the tool. A hole may be included to permit irrigation tubes and tool camera wires.

A tool tracking pattern 308, similar to the fixture tracking pattern 210, is disposed or formed on the tool pattern surface 306. The tool tracking pattern 308 is an optically visible pattern that is configured to provide visual reference points for externally mounted cameras to detect for use by a computer system to track the position and movement of the tool tracking assembly 300. The pattern shown in FIG. 10 could be used as the tool tracking pattern.

Figure 11:
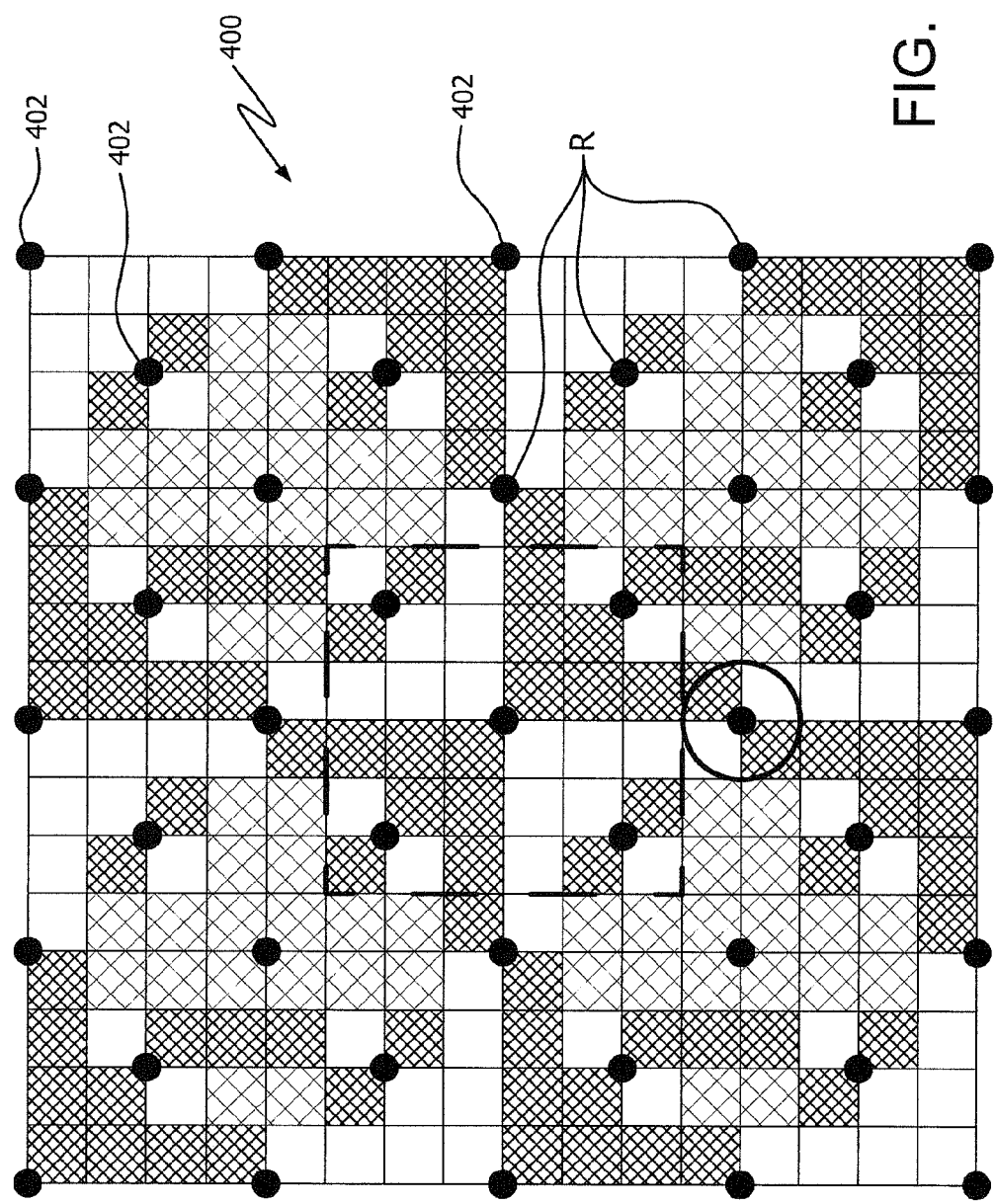
FIG. 11 is an illustration of a tracking tile with four tracking patterns arranged for unique tracking of the pattern.

Referring now to the FIG. 11, an embodiment of a tracking tile 400 is shown. In this embodiment, the tracking tile 400 includes a portion of the tracking pattern 210. More specifically, in the illustrated embodiment, when four tracking tiles are arranged as shown in FIG. 11, the intersection of the four tiles defines the tracking pattern 210 as indicated by the dashed lines. In the illustrated embodiment the lightly cross-hatched boxes can be either black or white within the scope of the invention. The choices of coloring of the lightly cross-hatched boxes, in combination with other boxes on the tile 400 permit the tile to be uniquely defined so that the pattern on the individual tile 400 is recognized by the system.

Figure 11A:
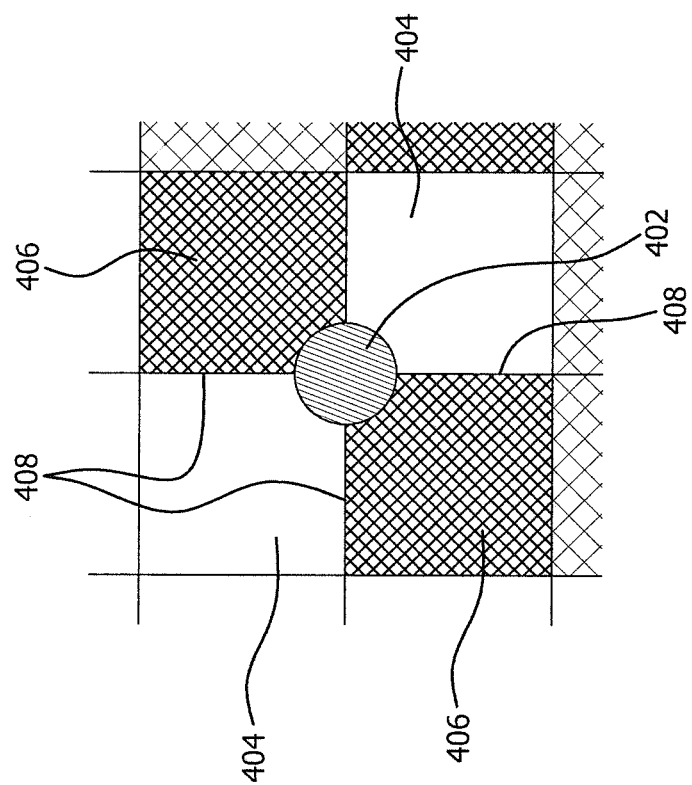
FIG. 11A is an enlarged view of a portion of the tracking pattern of FIG. 11.
Figure 12:
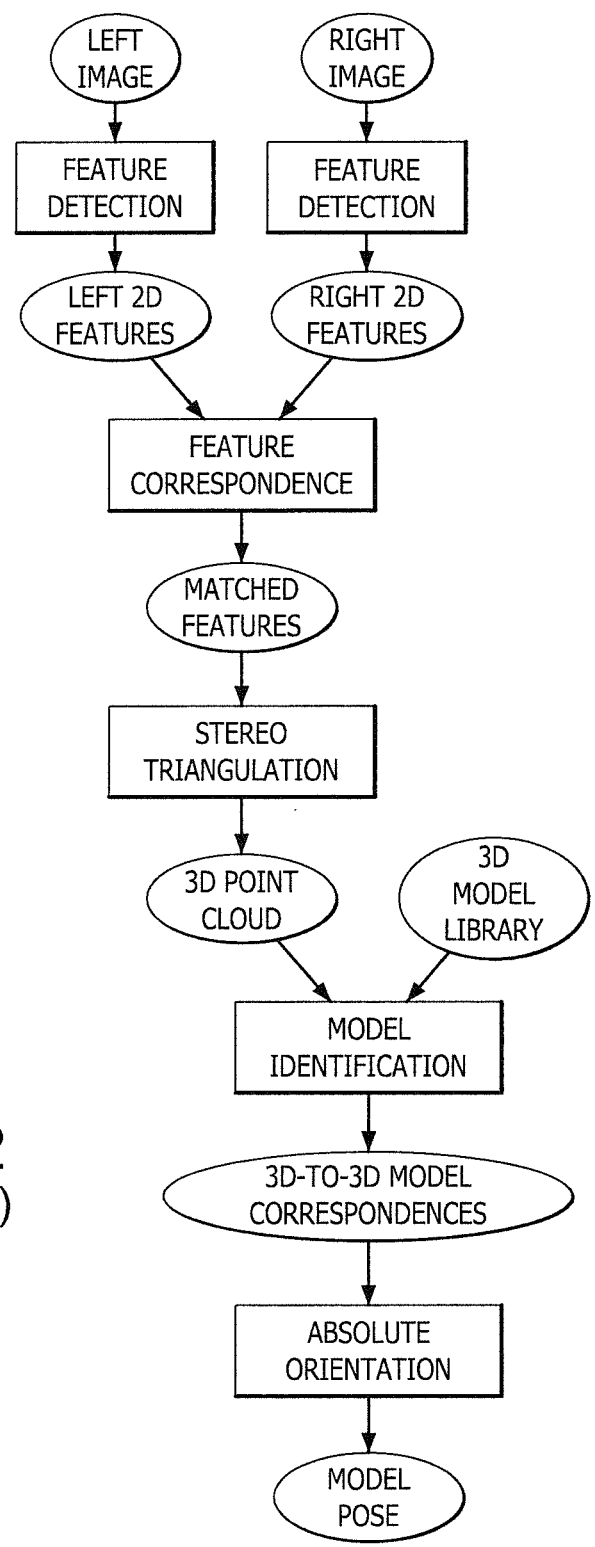
FIG. 12 is a flow chart illustrating a conventional method of determining model pose.

There are several benefits to using the tracking tile 400. First, each tile includes, on average, approximately 50% intensity (i.e., 50% light and 50% dark). This facilitates the ability of a computer system detecting, through a camera, the boxes in the tile by permitting the computer system to adjust the gain and exposure of the cameras in order to maximize detection performance. Also, when four tiles 400 are arranged as shown in FIG. 11, each tracking tile 400 includes a minimum of thirteen defined points 402, which in the preferred embodiment are x-corners, the center point of two intersecting lines between adjacent boxes of opposed color (i.e., black (dense cross-hatching) and white). The advantage of choosing x-corners as the defined points, is that location of the center point can be located to sub-pixel accuracy, and the location is stable under typical image degradations, in particular over-illumination and under-illumination and sensor noise, however it is contemplated that other types of defined points and combinations of different types of defined points can be used, for instance the centroids of circles or other shapes, and corner points on shapes with angled contrast regions. More particularly and with reference to FIG. 11A, which is an enlarged view of four adjacent boxes of opposed color, adjacent boxes of opposed colors (404 white, 406 black (dense cross-hatching)) are separated from one another by a line 408. In one embodiment, the system is programmed to detect two distinct colors, in this case, black and white, and locate a line between adjacent boxes of those two colors. For example, when the system detects two adjacent distinct colors it seeks a series of two or more adjacent points A, B between those distinct color boxes and defines a line 408 between the series of points A, B and, thus, between the two adjacent blocks 404, 406. The system analyses the pattern in order to detect four adjacent boxes of alternately distinct colors that form a square as shown in FIG. 11A. The intersection of the lines 408 between the boxes cross at a defined point 402. An alternate method for detecting an x-corner in an image is through analysis of the image structure tensor as in the Harris corner detector, well-known to those skilled in the art. In its broadest embodiment, each tile is any uniquely-identifiable (unambiguous) subset of a pattern. Also it is contemplated that tiles can overlap with other tiles, and do not need to be shaped as a series of squares, but can be oddly-shaped.

In embodiments with defined points that are not x-corners, an alternate detection algorithm, sensitive to the particular type of defined point can be used. For example, if the defined points include centroids of circular features, algorithms such as Laplacian of Gaussians, Difference of Gaussians, or Determinant of Hessians can be used.

As discussed above, the when four tiles 400 are arranged as shown in FIG. 11, each tracking tile 400 includes a minimum of thirteen defined points 402. The system includes a lookup table or stored data on a plurality of patterns, including size and arrangement (e.g., location) of boxes and defined points in the various patterns. The system also includes a transform (transformation matrix) for converting the pattern data to a target coordinate system. Preferably, the transform is a rigid body transform or a 3D affine transformation which includes 3D rotation, translation, scaling, and skew. It is contemplated that the transform can include non-linear deformations to conform the arrangement to a non-planar surface.

More specifically, in one embodiment, each tile has the following characteristics: (i) it contains a square grid of two (or more) distinct colors (preferably black and white), (ii) the defined points appear only at the grid locations (intersections), and (iii) are printed on a planar surface, which means that under perspective imaging (i.e., when observed in an arbitrary orientation by a camera recording an image), the tile appears deformed by a locally-affine transformation (meaning that the printed square tile will appear stretched and skewed into a rhombus shape in the image).

Figure 3:
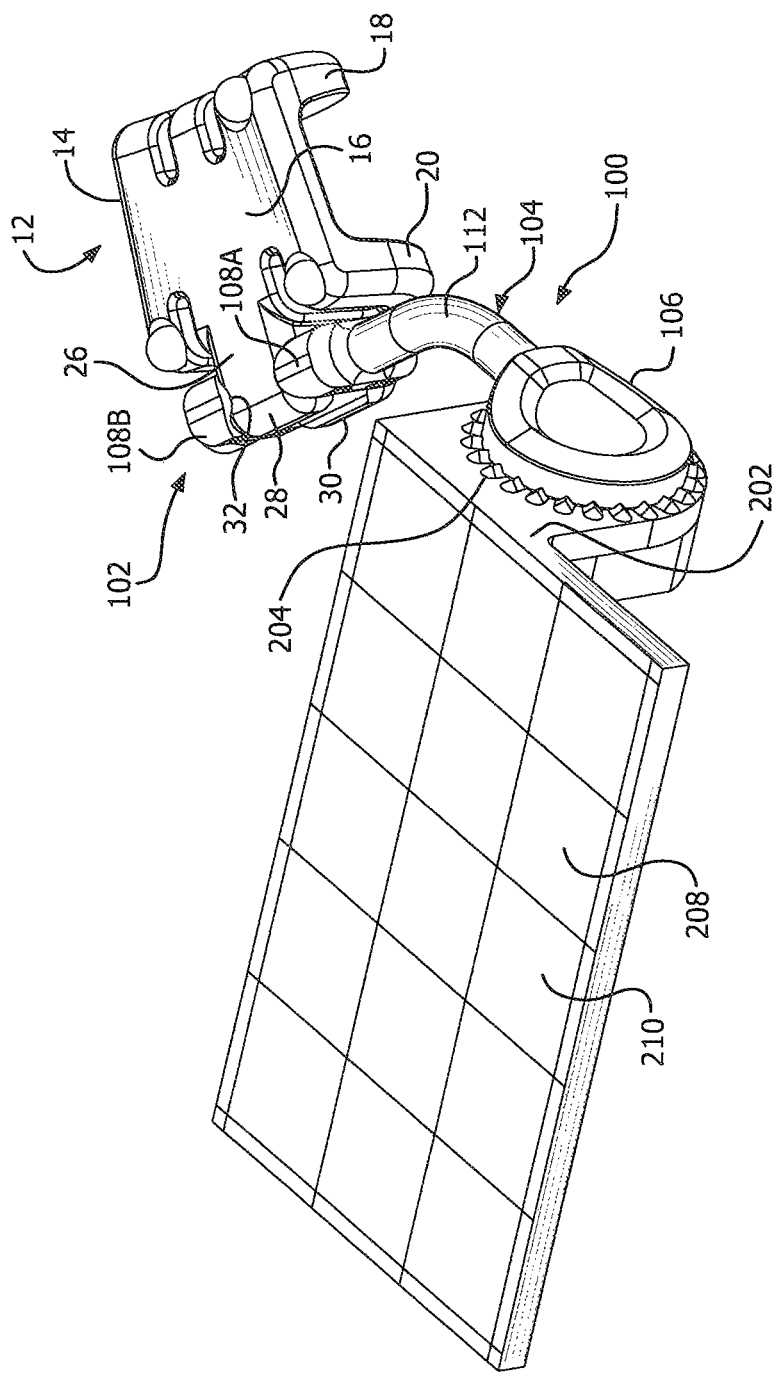
FIG. 3 is a perspective view of another embodiment of a tracking assembly with a pattern display surface attached to an oral fixture according to the present invention.

In the case where a planar tile is used (i.e., a tile where the grids are printed on a planar surface), such as the pattern tile arrangement in FIG. 3, each defined point is analyzed by the system as follows:

a. Adjacent defined points are located. More specifically, in one embodiment adjacent defined points can be a simple near neighbor (based on Euclidean distance) to the defined point. In another embodiment, the neighbor distance can be replaced by the distance along a high-contrast edge. Many other distance functions are contemplated b. Using the defined point being analyzed and the adjacent defined points, a pair of basis vectors between the defined point and two of its adjacent defined points is determined, c. The basis vectors are then used to compute a rectifying affine transform that will transform a rhombohedral image patch into a square image patch, three of whose corners are the defined point and its two adjacent defined points (i.e., a transform to convert the detected defined point locations in the image into the square grid used in a planar printed tile.)

d. The system then uses the affine transform, assuming that the three detected defined points are at the corner and edges of a tile, to predict where each grid location will be in the image (essentially creating an overlay on the image of the grid skewed according to the affine transform).

e. The image is analyzed at each predicted grid location to calculate a descriptor. A descriptor describes a local region. In one implementation, it is a 9×9 matrix representing a tile, where each element of the matrix is an x-corner type. The x-corner type applied to a local 2D coordinate system, i.e., the basis vectors define a local coordinate system which permit the defining of "right" and "up". In this coordinate system, if the image patch in the upper-left is bright (and the upper right is dark), the x-corner is left-oriented, if the opposite pattern appears, it's right-oriented. As such, each element of the matrix is either Left-Oriented, Right-Oriented, or no X-corner detected).

f. A score is then computed as to how closely the descriptor matches a stored encoding scheme. In the present invention, x-corners may be detected on parts of the scene that are not within the pattern. Likewise, many chosen combinations of three adjacent defined points may not in fact correspond to the tile corner and edges. In order to analyze for these false detections is to verify that the structure of the x-corner is consistent with the internal relationships defined by the encoding scheme that is chosen. In the preferred implementation, there are defined relationships between x-corners at various grid locations (e.g., each tile has four registration markers R at known locations (i.e., points where x-corners are guaranteed to occur due to the encoding scheme chosen), all have the same orientations as each of the four tile corners), that facilitate testing the hypothesis that the three features are at a tile corner and 2 adjacent tile edges, respectively. A registration marker is a portion of the tile that is constant no matter what the encoded identity of the unique tile is. Thus, there are pre-defined relationships between the elements of the 9×9 descriptor matrix. For example, in one implementation, the tile corners (elements [0,0]; [8,0]; [0,8]; [8,8] and the registration markers (elements [2,2]; [6,2]; [2,6]; [6,6]) are all the x-corners with the same x-corner type (left-oriented or right-oriented). Descriptors whose structure is inconsistent with these pre-defined relationships are rejected.

g. Once the system verifies that the known relationships are present, it can decode the encoded data in order to determine the identity of the observed tile.

In the case where the tiles are not formed planar but, instead, are defined or formed on a non-planar surface, e.g., the patterns are formed on a cylinder (FIG. 1) or a drill cone (FIG. 7), the above process of assuming the entire tile's grid is deformed by an affine transformation is no longer applicable. Instead, the system assumes that the tile is only locally-affine within a small sub-region of the tile, and varies from there in a smooth manner. The above steps (b)-(d) are modified to only predict nearby grid locations, i.e., grid locations that are close to a grid location where a grouping of x-corners has already been positively located. In one embodiment the nearby grid is within two grid units (using L-infinity distance) of a located x-corner. At this point, the system assumes the pattern is smoothly-varying enough that the affine assumption is valid when traversing the grid with only small corrections to the affine basis along the way. Thus, the system can process the planar tiles the same way as tiles that have curvature, by traversing the grid and correcting the affine basis along the way. On planar tiles, the corrections will effectively be zero. The basis vectors are computed about each subset of detected defined points in order to correct deviations from a purely affine assumption.

Once a set of descriptors has been computed for an image being analyzed, each descriptor is compared to a library of descriptors that are stored in the system and associated with a specific tile. For example, as discussed above, the matrix may include for each element −1 for left-oriented x-corner, 0 for no x-corner, 1 for right-oriented x-corner. In one embodiment, since each descriptor can be associated with several potential unique tiles, a score is calculated between each detected descriptor and each library descriptor, and the highest-scoring library matches are stored for each detected descriptor. The top scores can be processed further to determine the tile by using additional relevant information, e.g., where certain points should be located.

In an embodiment, the system includes or has access to a database of models of tracking patterns formed from one or more tiles. The present invention contemplates that the models can fall into two distinct arrangements of models. In the first arrangement, all the stored models have a unique subset of tiles where no tiles are repeated between models. In this case, knowing a single tile determines which model you're using. Each model is unique such that there is no replication of the arrangement of tiles between models. As such, the identification of the tile postulates a model pose. That is, each model in the model library contains a set of tiles that are members of the model.

In a second arrangement of models, a number of models would share the same tiles, but in different arrangements. As such, the system must generate a hypothesis for each model of which the detected tile is a member. In this case, detecting two or more tiles would help prove the correctness of the model. In either arrangement, since noise and other factors might impact the detection of x-corners, the particular model must be further analyzed (tested) as discussed below to confirm the model.

For each tile in a model, the database includes the 3D model locations for each point on the grid where defined points should appear. The identification of the tile or tiles in the image permits the system to select the model that applies to the image being observed, and allows a correspondence to be determined between at least the four tile corners in the image coordinates and the four 3D model locations of the tile corners. Through a conventional process of 3D pose estimation, the system estimates a rigid-body transform that defines the spatial relationship of the model in a camera-centric coordinate system from these at least four correspondences.

The system then preferably applies the remaining tiles in the selected model onto the image using the estimated rigid-body transform. These additional tiles are tested against the tile identification hypotheses, and a count of the number of hypotheses consistent with a given combination of model and rigid-body transform is aggregated. Only a model with a number of positively-identified tiles that exceed some threshold, for example, three correctly identified tiles, would be considered the proper model.

Once each camera reaches the end of this processing step, it is known which image defined points (and, consequently, which 2D image locations) correspond to which model defined points (and, consequently, which 3D model locations). Once both cameras have determined these correspondences, determining stereo feature correspondences is a matter of matching image features that correspond to common model defined points. This can be accomplished using known techniques. There is no need to apply epipolar constraints or pruning the resulting set of correspondences. This is because the defined points are positively identified with limited potential for spurious identification of a model, and no false correspondences.

Figure 13:
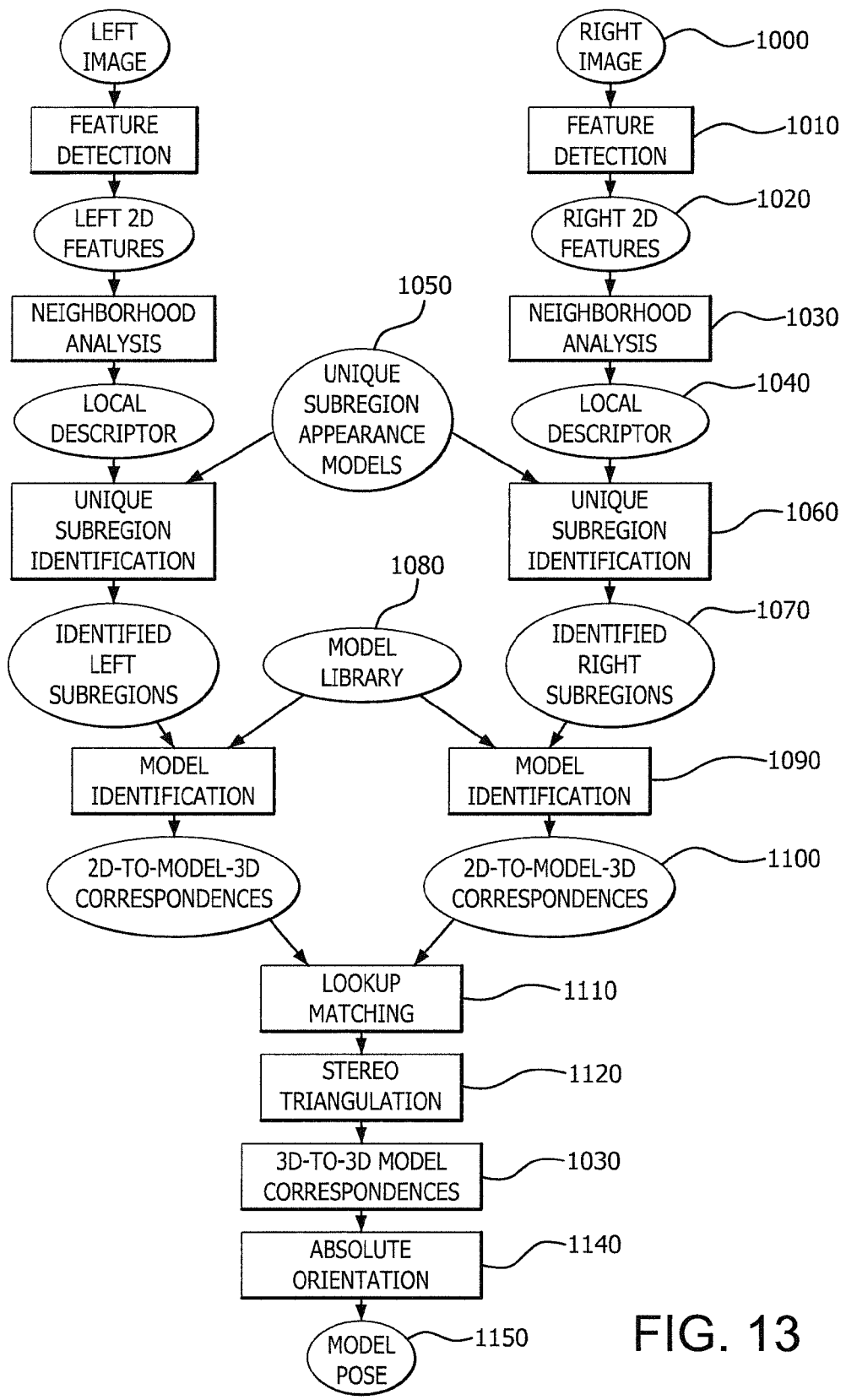
FIG. 13 is a flow chart illustrating a method of determining model pose according to the present invention.

As described above, using the transform the system is able to uniquely identify the model based on the defined points 402 on the tracking patterns 210, 308. Once that is performed, the stereo reconstruction is performed by triangulating the corresponding pair of image defined points using known techniques. This is shown in steps 1100, 1110, 1120 in FIG. 13. However, only image correspondences that are known to be good are passed in as input, and the association between reconstructed 3D points (in stereo tracker coordinates) and 3D model points is passed through this step. The output of lookup matching (step 1110) provides a 1:1 association between a set of pixel locations in the left image and a set of pixels in the right image. Through standard triangulation techniques using the known arrangement of the two cameras, each left/right pair of pixel locations are triangulated to generate an estimate of the 3D location of that feature in the scene. Each of these 3D coordinates are determined in a coordinate system fixed to the stereo tracking system (e.g., the left camera or right camera location, or the center between the cameras, can be used to define the origin and axes of the coordinate system). In contrast the 3D model points are defined in a model-centric coordinate system (e.g., the cone axis is the z axis, the center of the small end is (0,0,0).) Absolute orientation determines the transform between these two coordinate systems (tracker-centric and model-centric).

Once at least three correspondences between specific 3D tracker points (i.e., points in the tracker-centric coordinate system) and specific 3D model points (i.e., points in the model-centric coordinate system) are known (step 1130), conventional absolute orientation processes (step 1140) are used to determine the rigid-body transformation relating the tracker coordinate system to the model coordinate system, thereby determining the spatial location and orientation of the model in tracker coordinates (step 1150). As such, the pose of the tile 400 and the tracking patterns 210, 308 are tied to the model. The data is then used by the system to depict the actual movement of the oral fixture and tool fixture as movement of the associated models relative to scanned representation of the area of interest (e.g. the prior scanned image of the oral cavity).

The processes for forming the oral fixture 12, for scanning the location of fiducials on the fixture 12, and for registering the prior scanned image to actual video image are described in detail in U.S. patent application Ser. No. 14/209,500. Once the oral fixture 12 is formed, the bracket assembly 100 is attached to the flanges 28, 30 on the oral fixture 12 and to the fixture tracking assembly 200. The oral fixture 12 is attached to the appropriate teeth of the patient.

Figure 14:
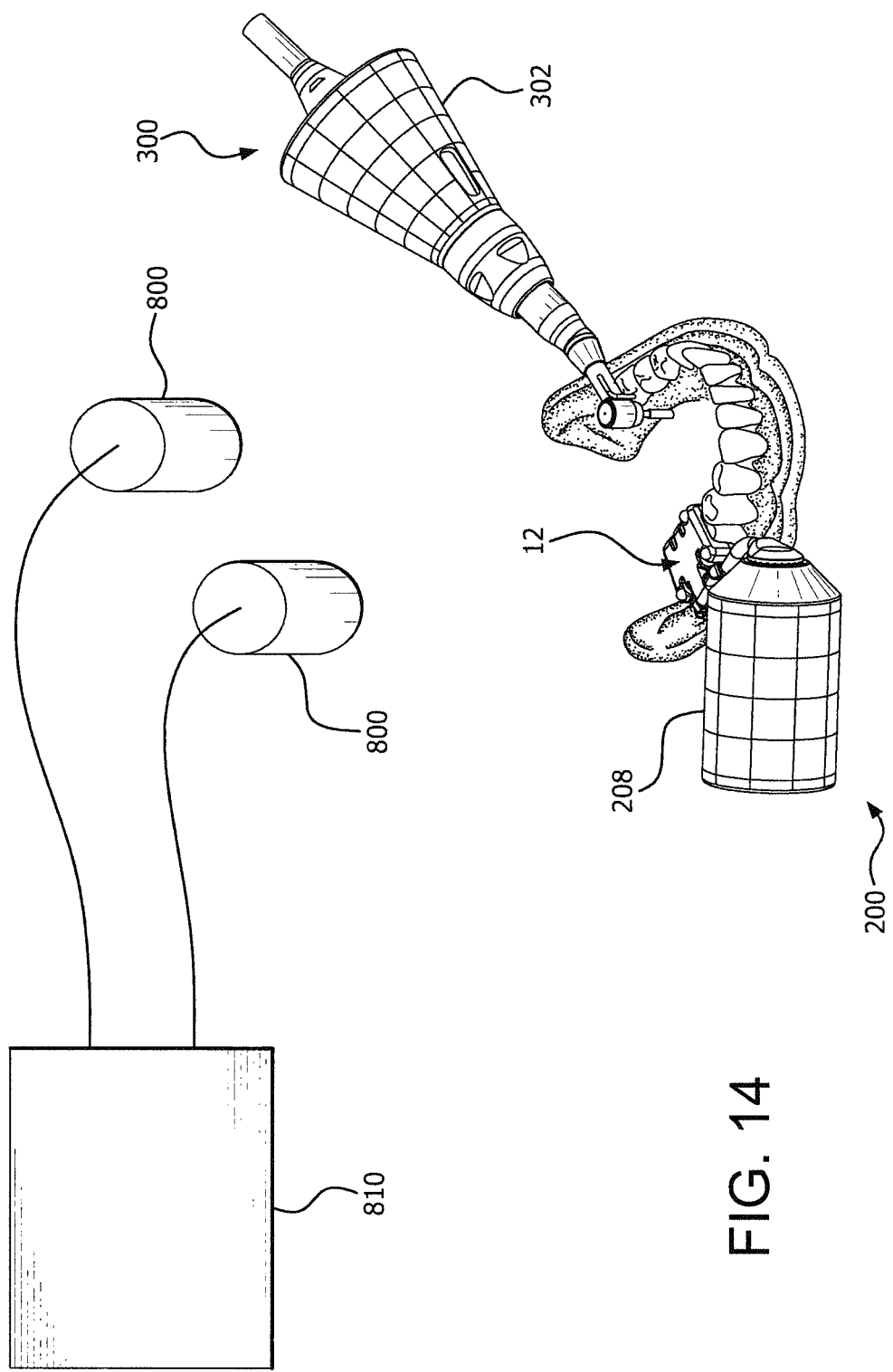
FIG. 14 is a schematic representation of an oral fixture and dental instrument with imaging cameras according to the present invention.

Referring to FIG. 14, in order to determine the location of the oral fixture 12 on the patient and the surgical tool 302, the present invention uses two external cameras 800 mounted in a location to view the fixture tracking pattern 210 and tool tracking pattern 308 and detect the defined points as described above. The data from the cameras 800 is transmitted to a processor 810 which conducts some or all of the processing described above and illustrated into FIG. 13. From that the system determines the position (pose) of the tracking patterns and their movement within a predetermined coordinate system. The system uses the location of the fiducial markers on the oral fixture 12 from the scanned image and their relationship to the fixture tracking assembly 200 for determining movement of the patient and the location of the tool fixture assembly 300 relative to the oral fixture 12, and then to calculate the location of the tool bit tip relative to the operation site.

The present invention provides significant advantages over the prior existing stereo tracking systems. First, the present invention preferably implements a significant number of computationally-expensive steps on each camera independently of the other cameras and the main processing system. This allows for easier scaling of the system, especially as the number of cameras in the system grows beyond two. In a conventional stereo tracking system the requirement of feature correspondence would grow as a function of $O(Nc^2)$ where Nc is the number of cameras used in a standard stereo tracking system.

It is contemplated that the processing could be carried out in a processor in the camera and the programming and data could be embedded in memory associated with the processor.

These cameras could be placed remotely on a distributed network. The resulting communication bandwidth would be a tiny fraction of the passing the images themselves, or even the set of image feature points that are required in conventional systems.

The rich nature of the identified tiles makes the potential for spurious identification of a model exceedingly remote, whereas significant numbers of features detected on non-model objects in the standard stereo tracking case can give rise to many spurious model identifications.

While the above description refers to the term "tile" as a uniquely-identifiable unit, which can be arranged to form an optical pattern, the term is not restricted to the conventional notion of "tiling" of such units as abutting and non-overlapping. Co-pending application Ser. No. 14/209,500 details an interleaved encoding scheme where multiple tiles overlap and occupy the same portion of a pattern in order to enhance two-scale detection. It is contemplated that even in a conventionally-tiled pattern, the arrangement of the unique tiles can be chosen such that each junction of 4 tiles forms another unique tile from the combination of portions of the tiles that are nearest the junction, in such a way that every patch on the pattern is a member of 2 or more tiles. Such a tiling would have the advantage that when portions of the pattern are obscured from view, a greater number of complete tiles should be visible to aid model identification. While the above description details tile boundaries with 90-degree corners it is further contemplated that the tile boundaries can contain arbitrary polyline or rounded segments. The two-scale encoding scheme in co-pending application Ser. No. 14/209,500 includes a combination of square tiles and complex tiles that have holes.

The calculations and programming techniques used for tracking and determining the motions of the various components are well known and, thus, no further information is necessary.

The foregoing embodiments are based on the assumption that the patient has sufficient teeth to mount the oral fixture 12 and fixture tracking assembly 200. If, however, the condition of the patient's mouth prevents attachment of either or both of the oral fixture 12 and fixture tracking assembly 200, the present invention envisions that either component can be directly mounted to the jaw bone of the patient.

While the above description refers to a surgical tool or instrument that includes a drill, the term "surgical instrument" or "surgical tool" is intended to cover other tools used during intraoral procedures, such as ablation tools for ablating tissue, including third molars in children.

The system or systems described herein may be implemented on any form of computer or computers and the components may be implemented as dedicated applications or in client-server architectures, including a web-based architecture, and can include functional programs, codes, and code segments. The system of the present invention may include a software program be stored on a computer and/or storage device (e.g., mediums), and/or may be executed through a network. The method may be implemented through program code or program modules stored on a storage medium.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The embodiments herein may be described in terms of various processing steps. Such processing steps may be realized by any number of hardware and/or software components that perform the specified functions. For example, the described embodiments may employ various integrated circuit components, e.g., memory elements, processing elements, logic elements, look-up tables, and the like, which may carry out a variety of functions under the control of one or more microprocessors or other control devices. Similarly, where the elements of the described embodiments are implemented using software programming or software elements the invention may be implemented with any programming or scripting language such as C, C++, Java, assembler, or the like, with the various algorithms being implemented with any combination of data structures, objects, processes, routines or other programming elements. Functional aspects may be implemented in algorithms that execute on one or more processors. Furthermore, the embodiments of the invention could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail.

Finally, the steps of all methods described herein are performable in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those skilled in this art without departing from the spirit and scope of the invention.

We claim:

1. An image guidance system for tracking a surgical instrument during oral surgery comprising:
    a fixture configured to be removably attached to a patient's anatomy in a location spaced apart from a surgical area;
    a first tracking assembly including a bracket assembly removably attached to the fixture and a first tracking pattern surface, the first tracking pattern surface including a first optically visible pattern, the bracket assembly positioning the first tracking pattern at a location spaced apart from the surgical area;
    a tool for use in the surgical procedure, the tool having a proximate tip end to which a drill bit is attached, an intermediate portion adapted to be held by a user, and a distal end opposite from the tip end;
    a second tracking assembly including a second tracking pattern surface mounted to the tool at a location spaced apart from the tip end of the tool so as to be spaced apart from the surgical area and positioned external to the oral cavity during use, the second tracking pattern surface including a second optically visible pattern;
    a plurality of cameras mounted at a location spaced apart from the surgical area and the first and second tracking assemblies at a position that permits the cameras, when activated, to capture images of the optically visible patterns on the first and second tracking pattern surfaces;
    a reference dataset including the location and orientation of the fixture with respect to a CT scan of the surgical area;
    a processing system to process the captured images and configured to recognize the optically visible patterns and triangulate the locations and orientations of the first and second tracking assemblies, the processing system determining the location and orientation of the tracked tool based on the reference dataset and analyzing relative transforms between each camera of the optically visible patterns on the first and second tracking pattern surfaces.

2. An image guidance system according to claim 1 wherein the fixture is configured to removably attach to opposite sides of one or more teeth in a patient's mouth without the need for tools for attaching and removing the fixture.

3. An image guidance system according to claim 1 wherein the bracket assembly includes a bracket mount that removably attaches to a flange on the fixture, a tracking mount that attaches to the first tracking pattern surface, and a support arm that attaches the bracket mount to the tracking mount.

4. An image guidance system according to claim 3 wherein the bracket mount includes two spaced apart mounting posts that engage with the flange.

5. An image guidance system according to claim 3 wherein the attachment of the tracking mount to the first tracking pattern surface is adjustable, the adjustable attachment of the tracking mount permitting angular adjustment of the first tracking pattern surface relative to the support arm.

6. An image guidance system according to claim 3 wherein the tracking mount includes a base with a series of indentations and protrusions.

7. An image guidance system according to claim 6 wherein the first tracking assembly includes a frame with an attachment to the tracking mount, the attachment being configured to permit the frame to be adjustable with respect to the bracket assembly.

8. An image guidance system according to claim 7 wherein the frame includes a series of indentations and protrusions that are configured to mate with the indentations and protrusions on the tracking mount so as to permit the rotational orientation of the tracking frame relative to the base to be adjustable.

9. An image guidance system according to claim 1 wherein the optically visible patterns each contain a plurality of 2D contrasting shapes, the contrasting shapes arranged so as to uniquely differentiate each optically visible pattern from the other optically visible pattern.

10. An image guidance system according to claim 9 wherein each camera is located so as to capture at least a portion of the optically visible pattern on each of the first and second tracking pattern surfaces such that the image of each optically visible pattern captured by the camera is at a different viewing angle than the image of the same optically visible pattern captured by the other camera(s), the cameras configured to send to the processor data representative of the 2D images of the optically visible patterns captured by the cameras.

11. An image guidance system according to claim 10 wherein the processor includes a dataset of patterns, including location data for contrasting shapes on each of the patterns in the dataset, and wherein the processor is configured to analyze the dataset of patterns to determine which of the patterns in the dataset corresponds to each of the optically visible patterns in the 2D images received from the cameras.

12. An image guidance system according to claim 11, wherein the contrasting shapes include adjacent boxes of distinct color, each set of adjacent boxes being separated from one another by a line, and wherein a defined point is formed by a center point of two intersecting lines, and wherein the processor determines the location of defined points in the dataset of patterns and the optically visible patterns for determining whether a given pattern from the dataset of patterns corresponds to the optically visible patterns.

13. An image guidance system for tracking a surgical instrument during oral surgery comprising:
    a fixture configured to be removably attached to a patient's anatomy in an oral cavity at a location spaced apart from a surgical area;
    a first tracking assembly including a bracket assembly having a first end adjustably attached to the fixture and extending away from the oral cavity, the bracket assembly having a second end attached to a first tracking pattern surface, the bracket assembly permitting the first tracking pattern to be adjustable with respect to the fixture, the first tracking pattern surface including a first optically visible pattern, the bracket assembly positioning the first tracking pattern at a location spaced apart from the oral cavity;
    a surgical tool for use in the surgical procedure, the tool having a proximate tip end, an intermediate portion adapted to be held by a user, and a distal end opposite from the tip end;
    a second tracking assembly including a second tracking pattern surface, the second tracking assembly configured to mount to a surgical tool for use in the oral surgery at a location spaced apart from the tip end of the tool so as to be spaced apart from the surgical area and positioned external to the oral cavity during use, the second tracking pattern surface including a second optically visible pattern;
    a plurality of cameras mounted at a location spaced apart from the surgical area and the first and second tracking assemblies at a position that permits the cameras, when activated, to detect images of the optically visible patterns on the first and second tracking pattern surfaces;

a reference dataset including the location and orientation of the fixture with respect to a CT scan of the oral cavity; and a processing system to process the captured images and configured to recognize the optically visible patterns and triangulate the locations and orientations of the first and second tracking assemblies, the processing system determining the location and orientation of the tracked tool based on the reference dataset and analyzing relative transforms between each camera of the optically visible patterns on the first and second tracking pattern surfaces.

14. An image guidance system according to claim 13 wherein the fixture is configured to removably attach to opposite sides of one or more teeth in a patient's mouth without the need for tools for attaching and removing the fixture, wherein the bracket assembly includes a bracket mount that removably attaches to a flange on the fixture, a tracking mount that attaches to the first tracking pattern surface, and a support arm that attaches the bracket mount to the tracking mount, wherein the attachment of the tracking mount to the first tracking pattern surface is adjustable, the adjustable attachment of the tracking mount permitting angular adjustment of the first tracking pattern surface relative to the support arm.

15. An image guidance system according to claim 14 wherein the tracking mount includes a base with a series of indentations and protrusions, the first tracking assembly including a frame with an attachment to the tracking mount, the attachment being configured to permit the frame to be adjustable with respect to the bracket assembly, and wherein the frame includes a series of indentations and protrusions that are configured to mate with the indentations and protrusions on the tracking mount so as to permit the rotational orientation of the tracking frame relative to the base to be adjustable.

16. An image guidance system according to claim 13 wherein the optically visible patterns each contain a plurality of 2D contrasting shapes, the contrasting shapes arranged so as to uniquely differentiate each optically visible pattern from the other optically visible pattern, and wherein each camera is located so as to capture at least a portion of the optically visible pattern on each of the first and second tracking pattern surfaces such that the image of each optically visible pattern captured by the camera is at a different viewing angle than the image of the same optically visible pattern captured by the other camera(s), the cameras configured to send to the processor data representative of the 2D images of the optically visible patterns captured by the cameras.

17. An image guidance system according to claim 16, wherein the processor includes a dataset of patterns, including location data for contrasting shapes on each of the patterns, and wherein the processor is configured to analyze the dataset of patterns to determine which of the patterns in the dataset corresponds to each of the optically visible patterns in the 2D images received from the cameras.

18. An image guidance system according to claim 17, wherein the contrasting shapes include adjacent boxes of distinct color, each set of adjacent boxes being separated from one another by a line, and wherein a defined point is formed by a center point of two intersecting lines, and wherein the processor determines the location of defined points in the dataset of patterns and the optically visible patterns for determining whether a given pattern from the dataset of patterns corresponds to the optically visible patterns.

19. An image guidance system according to claim 1, wherein the second tracking pattern surface is mounted to an external portion of the tool so as to position the visible pattern in a field of view of the cameras.

* * * * *